(12) United States Patent
Eichhorn et al.

(10) Patent No.: US 12,391,965 B2
(45) Date of Patent: Aug. 19, 2025

(54) CONVERSION OF FARNESYLACETONE TO HOMOFARNESYLACETATE BY BAEYER-VILLIGER MONOOXYGENASE

(71) Applicant: Givaudan SA, Vernier (CH)

(72) Inventors: Eric Eichhorn, Zürich (CH); Andreas Goeke, Duebendorf (CH)

(73) Assignee: GIVAUDAN SA, Vernier (CH)

( * ) Notice: Subject to any disclaimer, the term of this patent is extended or adjusted under 35 U.S.C. 154(b) by 422 days.

(21) Appl. No.: 17/998,540

(22) PCT Filed: Jun. 30, 2021

(86) PCT No.: PCT/EP2021/067983
§ 371 (c)(1),
(2) Date: Nov. 11, 2022

(87) PCT Pub. No.: WO2022/003017
PCT Pub. Date: Jan. 6, 2022

(65) Prior Publication Data
US 2023/0203548 A1    Jun. 29, 2023

(30) Foreign Application Priority Data
Jul. 1, 2020 (GB) .................... 2010072

(51) Int. Cl.
*C12P 7/54* (2006.01)
*C12N 9/02* (2006.01)
*C12P 7/04* (2006.01)

(52) U.S. Cl.
CPC .............. *C12P 7/54* (2013.01); *C12N 9/0073* (2013.01); *C12P 7/04* (2013.01)

(58) Field of Classification Search
CPC .................... C12P 7/54; C12P 7/04
See application file for complete search history.

(56) References Cited

FOREIGN PATENT DOCUMENTS

| WO | 9206063 A2 | 4/1992 |
|---|---|---|
| WO | 2013156398 A1 | 10/2013 |
| WO | 2013179005 A1 | 12/2013 |
| WO | 2014096850 A1 | 6/2014 |
| WO | 2021110858 A1 | 6/2021 |

OTHER PUBLICATIONS

International Search Report for App. No. PCT/EP2021/067983 dated Oct. 25, 2021.
Written Opinion for App. No. PCT/EP2021/067983 dated Oct. 25, 2021.
Great Britain Search Report for App. No. 2010072.3 dated Dec. 15, 2020.
Anett Kirschner, et al., Cloning, expression, and characterization of a Baeyer-Villiger monozygenase from Pseudomonas fluorescens DSM 50106 in *E. coli*, Biotechnologically Relevant Enzymes and Proteins, Applied Microbiology Biotechnology, Aug. 31, 2006, pp. 1065-1072, vol. 73, Springer.
Jessica Rehdor, et al., Cloning, expression and characterization of a Baeyer-Villiger monoozygenase from Pseudomonas putida KT2440, Biotechnology Letters, May 26, 2007, pp. 1393-1398, vol. 29, Springer.
Ana Rioz-Martinez, et al., Biocatalyzed concurrent production of enantioenriched compounds through parallel interconnected kinetic asymmetric transformations, Organic & Biomolecular Chemistry, Jan. 22, 2010, pp. 1431-1437, vol. 8, The Royal Society of Chemistry 2010.
Yong Cheol Park, et al., Microbial formation of esters, Applied Microbiology Technology, Aug. 28, 2009, pp. 13-25, vol. 85, Springer.
Hannes Leisch, et al., Baeyer-Villiger Monooxygenases: More Than Just Green Chemistry, Chemical Reviews, 2011, pp. 4165-4222, vol. 111, ACS Publications.
Daoyi Guo, et al., Biosynthesis of advanced biofuel farnesyl acetate using engineered *Escherichia coli*, Bioresource Technology, Aug. 29, 2018, pp. 577-580, vol. 269, Elsevier.
Alejandro F. Barrero, et al., Synthesis of ( )-Ambrox from (E)-Nerolidol and Beta-Ionone via Allylic Alcohol [2,3] Sigmatropic Rearrangement, The Journal of Organic Chemistry, 1996, pp. 2215-2218, vol. 61, American Chemical Society.
Philip Kocienski, et al., A Highly Selective and Iterative Approach to Isoprenoid Chains: Synthesis of Homogeraniol, Homofarnesol, and Homogeranylgeraniol, The Journal of Organic Chemistry, 1989, pp. 1215-1217, vol. 54, Issue 5.
Marco W. Fraaije, et al., The Prodrug Activator EtaA from *Mycobacterium tuberculosis* is a Baeyer-Villiger Monozygenase, The Journal of Biological Chemistry, Nov. 10, 2003, pp. 3354-3360, vol. 279, Issue 5, The American Society for Biochemistry and Molecular Biology, Inc.

*Primary Examiner* — Tekchand Saidha
(74) *Attorney, Agent, or Firm* — CURATOLO SIDOTI & TRILLIS CO., LPA; Floyd Trillis, III; Salvatore A. Sidoti

(57) ABSTRACT

An enzyme-mediated method for the production of acetates as defined by formula (I), the products of said method, and uses of said products.

13 Claims, 1 Drawing Sheet

CONVERSION OF FARNESYLACETONE TO HOMOFARNESYLACETATE BY BAEYER-VILLIGER MONOOXYGENASE

CROSS REFERENCE TO RELATED APPLICATIONS

This application is a national stage application of International Application No. PCT/EP2021/067983, filed 30 Jun. 2021, which claims priority from Great Britain Patent Application No. 2010072.3, filed 1 Jul. 2020, both of which applications are incorporated herein by reference.

TECHNICAL FIELD

The present invention relates to a new process for the preparation of homofarnesol, in particular of (3E,7E)-homofarnesol, and the ethyl derivative thereof.

BACKGROUND

Homofarnesol is an important intermediate for the production of (−)-Ambrox (3a,6,6,9a-tetramethyldodecahydronaphtho[2,1-b]furan), a sought-after fragrance ingredient. The literature describes various processes for the preparation of homofarnesol. For example, homofarnesol is synthesized in a lengthy process starting from Nerolidol (3,7,11-trimethyldodeca-1,6,10-trien-3-ol), via homofarnesylic acid amid (A. F. Barrero et al., J. Org. Chem. 1996, 61, 2215). Alternatively, homofarnesol may be prepared by decarbonylation of Nerolidol in the presence of a polar solvent and a palladium halide catalyst (WO92/06063). Another way for the production of homofarnesol has been described by P. Kociensiki et al. (J. Org. Chem. 1989, 54, 1215), starting from dihydrofuran over five stages via homogeraniol. Recently, the synthesis of homofarnesol from geranylacetone via Wittig olefination, followed by cyclopropane ring opening and formyloxylation has been described in the literature (WO2013/156398).

All hitherto known methods have disadvantages, for example, the used reagents are expensive, process conditions are economically unattractive (e.g., temperature below 0° C., used reagents are toxic, and/or used solvents are flammable.

It is therefore desirable to provide new or improved methods for making homofarnesol and ethylhomofarnesol and/or a precursor thereof.

SUMMARY OF THE INVENTION

In accordance with a first aspect of the present invention there is provided a method of producing an acetate of formula (I)

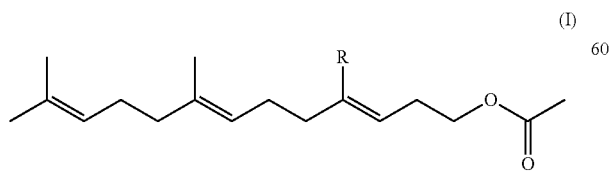

(I)

wherein R is methyl or ethyl, from a ketone of formula (II)

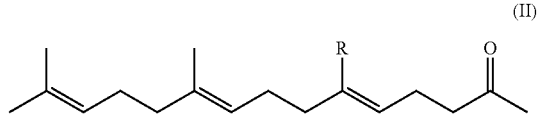

(II)

wherein R has the meaning given above, the method comprising contacting the compound of formula (II) with a Baeyer-Villiger monooxygenase (BVMO) enzyme in the presence of a cofactor.

In accordance with a second aspect of the present invention there is provided a method of producing by hydrolysis an alcohol of formula (III)

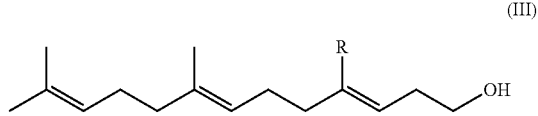

(III)

wherein R is methyl or ethyl, from an acetate of formula (I) obtained by the method of the first aspect of the invention.

In accordance with a third aspect of the present invention there is provided the use of the acetate of formula (I) obtained by and/or obtainable by the method of the first aspect of the present invention as precursor for the generation of an alcohol of formula (III), which optionally is used as the substrate for an enzyme-mediated production of a fragrance ingredient.

Certain embodiments of any aspect of the present invention may provide one or more of the following advantages:
  Unusual and novel biological route to a precursor of homofarnesol/ethylhomofarnesol,
  The use of enzyme technology for the implementation of green chemistry and environmentally friendly synthetic processes.

The details, examples and preferences provided in relation to any particular one or more of the stated aspects of the present invention will be further described herein and apply equally to all aspects of the present invention. Any combination of the embodiments, examples and preferences described herein in all possible variations thereof is encompassed by the present invention unless otherwise indicated herein, or otherwise clearly contradicted by context.

DETAILED DESCRIPTION

Figure 1:
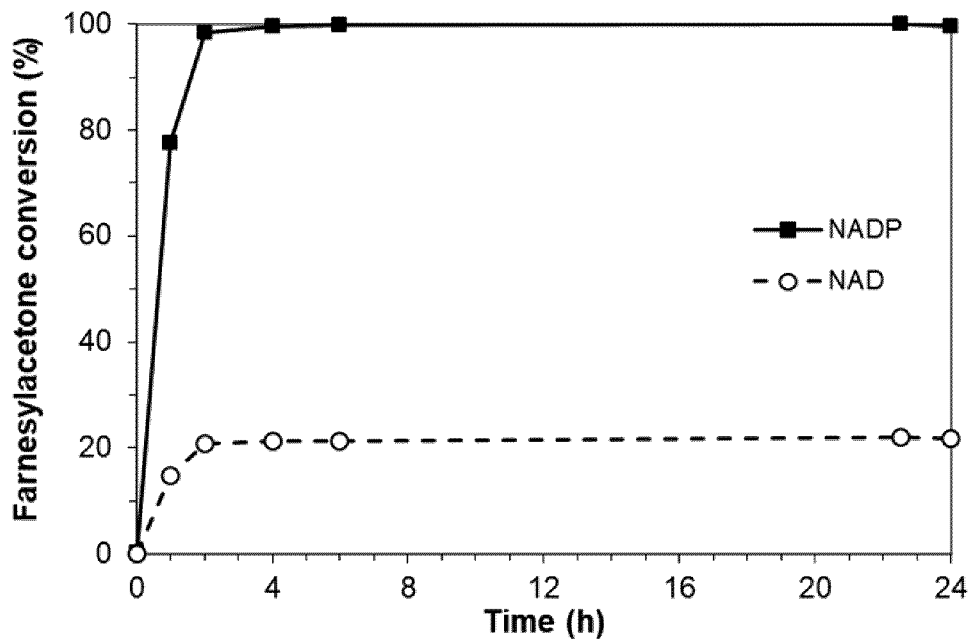
FIG. 1 shows the conversion over time of farnesylacetone in the presence of NAD or NADP in combination with a Glucose Dehydrogenase enzyme.

The present invention is based on the surprising finding that a ketone of formula (II) having a linear alkene chain undergoes an oxidation in the presence of a Baeyer-Villiger monooxygenase (BVMO) enzyme, resulting in an acetate, which can be used as a precursor for the preparation of an alcohol, such as homofarnesol or ethylhomofarnesol.

It is known that BVMO enzymes can catalyse the conversion of ketones to esters. However, those enzymes that are reported are only described as acting in biological systems on cyclic substrates (including terpenones and benzo-fused ketones), aliphatic ketones, and aliphatic hydroxyketones. Surprisingly, it was now found that the conversion of polyunsaturated branched ketones as defined by formula (II) to acetates of formula (I) are also catalysed by BVMO enzymes. Nowhere in the literature is it reported that BVMO enzymes could act on polyunsaturated branched ketones.

There is therefore provided herein a method of producing an acetate of formula (I)

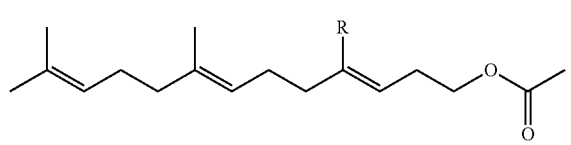

(I)

wherein R is methyl or ethyl,
from a ketone of formula (II)

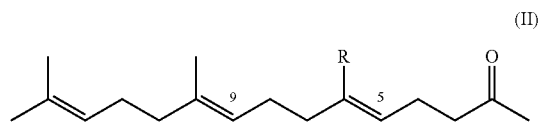

(II)

wherein R has the meaning given above,
the method comprising contacting the compound of formula (II) with a Baeyer-Villiger monooxygenase (BVMO) enzyme in the presence of a cofactor.

The compound of formula (II) exists in the form of four different stereoisomers, for example, as a compound of formula (II) having an 5E,9E- or 5Z,9E-configuration.

In certain embodiments, the method comprises contacting an 5E,9E-compound of formula (II) with a BVMO enzyme in the absence of any other stereoisomers of formula (II).

In other embodiments, the compound of formula (II) may, for example, be a mixture of stereoisomers. In certain embodiments, the mixture comprises the 5E,9E-compound of formula (II) and one or more other stereoisomers of formula (II).

In certain embodiments, the mixture comprises the 5E,9E-compound of formula (II) and the 5E,9Z-compound of formula (II).

In certain embodiment, the mixture comprises the 5E,9E-compound of formula (II) as main component. By main component is meant that the weight % of 5E,9E-compound present in the mixture is greater than the weight % of 5Z,9E-compound of formula (II).

When R is methyl, the compound of formula (II) may be referred to as farnesylacetone, encompassing E,E-farnesylacetone, E,Z-farnesylacetone, Z,E-farnesylacetone, Z,Z-farnesylacetone, and mixtures thereof.

When R is ethyl, the compound of formula (II) may be referred to as ethylfarnesylacetone, encompassing E,E-ethylfarnesylacetone, E,Z-ethylfarnesylacetone, Z,E-ethylfarnesylacetone, Z,Z-ethylfarnesylacetone, and mixtures thereof.

The compound of formula (II) wherein R is methyl is commercially available. The compound of formula (II) wherein R is ethyl is novel in its own right. It may be synthesized from 5,9-dimethyldeca-4,8-dienal following the procedure as described in Example 11.

The term "BVMO (Baeyer-Villiger monooxygenase)", as used herein, refers to a monooxygenase which can catalyze various oxidation reactions, including a Baeyer-Villiger oxidation for the production of an ester compound of formula (I) by oxidation of ketone of formula (II).

The BVMO enzyme may be a wild type enzyme, or a modified enzyme. The term "wild type" as used herein whether with reference to polypeptides such as enzymes, polynucleotides such as genes, organisms, cells, or any other matter refers to the naturally occurring form of said matter. The term "modified" as used herein with reference to polypeptides such as enzymes, polynucleotides such as genes, organisms, cells, or any other matter refers to such matter as being different to the wild type. Suitable alterations to wild type matter that may produce modified matter include alterations to the genetic material, alterations to the protein material. Alterations to the genetic material may include any genetic modification known in the art which will render the material different to the wild type. Examples of such genetic modifications include, but are not limited to: deletions, insertions, substitutions, fusions etc. which may be performed on the polynucleotide/s sequence containing the relevant gene or genes to be modified.

With respect to the objects of the present invention, as long as the BVMO enzyme is produced in the host cell and is capable of catalyzing the reaction of producing an acetate of formula (I) having an ester group introduced into the chain thereof from the ketone of formula (II) (e.g., homofarnesylacetate from farnesylacetone), the BVMO may be, but is not particularly limited to, a BVMO derived from a microorganism such as *Pseudomonas* sp., *Rhodococcus* sp., *Brevibacterium* sp., Comanonas sp., *Acinetobacter* sp., *Arthrobacter* sp., *Brachymonas* sp., Themobifida sp., *Gordonia* sp., Pseudooceanicola sp., etc., more preferably, BVMO derived from *Pseudomonas* sp., *Brachymonas* sp., Pseudooceanicola sp., or *Acinetobacter* sp., and most preferably, BVMO derived from *Acinetobacter* sp., *Pseudomonas* sp. (e.g. *Pseudomonas veronii*), *Brachymonas* sp. (e.g. *Brachymonas* petroleovorans) or Pseudooceanicola sp. (e.g. Pseudooceanicola batsensis). In one particular embodiment the BVMO is derived from *Acinetobacter* sp., or *Pseudomonas* sp. (e.g. *Pseudomonas veronii*). The nucleotide sequence of the BVMO-encoding gene can be obtained from the known database such as GenBank at NCBI.

Enzymes may also be defined by their function according to the EC classification. The Enzyme Commission number (EC number) is a numerical classification scheme for enzymes, based on the chemical reactions they catalyse. The BVMO suitable for carrying out the conversion described herein may, for example, belong to the EC 1.4.13 class (oxidoreductases acting on paired donors, with incorporation or reduction of molecular oxygen with NADH or NADPH as one donor, and incorporation of one atom of oxygen into the other donor).

The BVMO may, for example, be one or more of the BVMO enzymes used in the Examples below, for example EW-103 (which is a variant of a wild type *Acinetobacter* sp. BVMO enzyme) obtained from EnzymeWorks, Inc., San Diego (USA), or MekA obtained from Gecco Biotech B.V.

Baeyer-Villiger monooxygenase cofactors (BVMO-cofactors) are cofactors that assist the BVMO enzyme during the catalysis of reactions. The BVMO-cofactor used in the method provided herein may be of any type suitable for assisting the conversion of the ketone of formula (II) to the acetate of formula (I). The cofactor may, for example, be an inorganic or organic molecule. The BVMO-cofactor may, for example, be selected from nicotinamide adenine dinucleotide (NADH), and nicotinamide adenine dinucleotide phosphate (NADPH), or a combination thereof.

Preferably, the BVMO-cofactor is present in the reaction mixture at a starting molar concentration relative to BVMO such as the BVMO enzyme is saturated with NAD(P)H. Therefore, preferably the NAD(P)H is present in the reaction mixture at a concentration which is at least equal to the concentration of the BVMO enzyme.

In one embodiment of the present invention, the NAD (P)H is present in the reaction mixture at a starting concentration of about 1 to 10 mg/ml, e.g. between 1 to 5 mg/ml, or between 1 to 4 mg/ml.

Typically, cofactors are too expensive to be used in stoichiometric amounts, and it is desired to regenerate them. Furthermore, by regenerating the cofactor, it is possible to enhance the efficiency of the desired conversion or to facilitate product isolation, thereby further reducing the costs of the process. For this reason cofactor regeneration systems are often used.

Glucose dehydrogenase (GDH) enzymes are common for the regeneration of NAD(P)H. For example, GDH enzymes are commercially available from Codexis Inc. (GDH-105, GDH-901, CDX-019), Johnson Matthey (GDH-101) or EnzymeWorks (GDH-EW). Further GDH enzymes can be obtained according to literature, for example glucose dehydrogenase from *Bacillus subtilis*: (UniProtKB accession number: P12310, E.C. 1.1.1.47, (1986) J. Bacteriol. 1986, 166, 238-43). GDH enzymes are in general used in combination with, e.g., glucose for cofactor regeneration. Alternatively, alcohol dehydrogenase (ADH) enzymes can be used for cofactor regeneration, when combined with, e.g., isopropanol, if not interfering with the reaction catalyzed by a particular BVMO enzyme.

Other enzymes that can be used in cofactor regeneration are, for example, Phosphite dehydrogenase (PTDH) in combination with, e.g., sodium phosphite.

The Baeyer-Villiger monooxygenase may be present in the reaction mixture in any suitable form known in the art, such as but not limited to: a cell-free extract, or contained within the host organism cells, and these may be located within the reaction mixture in any suitable way known in the art, such as but not limited to: in free form in solution/suspension, or in purified and/or immobilized form (held upon a membrane, or bound to/within a column). Preferably the BVMO is present in the reaction mixture at a concentration necessary to produce the required amount of the acetate of formula (I) capable of being produced at the relative level of dissolved oxygen.

In one embodiment, the Baeyer-Villiger monooxygenase is present in the reaction mixture as a cell extract prepared from the cells it was produced in, wherein the cell is preferably the bacterial host cell used to produce the BVMO enzyme. The cell extract may be obtained by any suitable means capable of lysing the host cells, including, but not limited to: sonication, RNAse/lysozyme treatment, freeze-thaw treatment, or alkaline treatment.

Preferably the cell extract is then treated to remove cellular debris before being used as a source of Baeyer-Villiger monooxygenase in the method described herein. The cell lysate may be treated by any suitable means known in the art, including, but not limited to: filtration, centrifugation, or purification with salts to obtain a cleared cell extract.

The cofactor regeneration system serves to regenerate the BVMO-cofactor after it has been used to assist the conversion of the ketone of formula (II) to the acetate of formula (I). The cofactor regeneration system may, for example, regenerate the reduced form of the cofactor, for example NADH and/or NADPH. The cofactor regeneration system used in the methods provided herein may be of any type suitable for regenerating a BVMO-cofactor that is useful in the conversion of the ketone of formula (II) to the acetate of formula (I) (e.g. farnesylacetone to homofarnesylacetate) by a BVMO enzyme.

Thus, there is provided in a further aspect a method of producing an acetate of formula (I) from ketone of formula (II), the method comprising contacting the ketone of formula (II) with a BVMO enzyme in the presence of cofactor and a cofactor regeneration system.

In one specific embodiment, the cofactor regeneration system is an ADH/isopropanol cofactor regeneration system.

In another specific embodiment, the cofactor regeneration system is a GDH/Glucose cofactor regeneration system.

In another specific embodiment, the cofactor regeneration system is a Phosphite Dehydrogenase/Phosphite cofactor regeneration system.

The use of an ADH/isopropanol cofactor regeneration system has the advantage, compared to the GDH/Glucose system, that there is no acidification of the reaction medium.

The method of producing an acetate of formula (I) from a ketone of formula (II) is carried out under conditions of time, temperature, pH and solubilizing agent which allow for the conversion of the ketone of formula (II) to an acetate of formula (I).

The pH of the reaction mixture may be in the range of 4-9, preferably, 7 to 9 (which includes a pH of about 8.5) and can be maintained by the addition of buffers to the reaction mixture or pH correction. An exemplary buffer for this purpose is a Tris-HCl buffer, or Glycine/NaOH buffer.

The temperature is between from about 15° C. to about 60° C., for example from about 15° C. to about 50° C. or from about 15° C. to about 45° C. or from about 30° C. to about 60° C. or from about 35° C. to about 55° C. for the BVMO enzyme considered. The temperature can be kept constant or can be altered during the bioconversion process.

The method provided herein may further comprise purification of the compound of formula (I) and/or separation from any unreacted compound of formula (II). For example the compound of formula (I) may be purified by solvent extraction (e.g. using methyl benzene, hexane, tert. Butyl-methylether (tBME)) and/or distillation.

In a further aspect of the present invention, the compound of formula (I) may be further reacted. For example, the compound of formula (I) may be hydrolysed to a compound of formula (III)

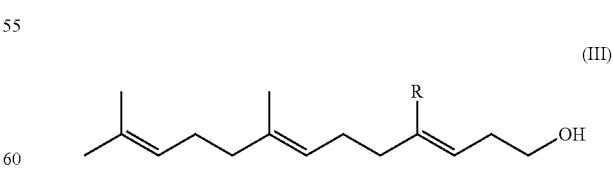

(III)

wherein R is methyl or ethyl.

In certain embodiments, the hydrolysis may be biocatalysed, and optionally take place in the same reaction broth.

Alternatively, the compound of formula (I) can be chemically hydrolysed, preferably after the purification, e.g. in methanolic solution in the presence of potassium carbonate.

The thus obtained alcohol may be used, for example, as a substrate for a biocatalysed conversion.

In certain embodiments, the compound of formula (III) wherein R is methyl may be converted to (−)-Ambrox in the presence of an SHC (Squalene Hopene Cyclase) enzyme.

In certain embodiments, the compound of formula (III) wherein R is ethyl may be converted to Ethylambrofix (which is described in more details in WO2021/110858).

The examples described herein are illustrative of the present disclosure and are not intended to be limitations thereon. Different embodiments of the present disclosure have been described according to the present disclosure. Many modifications and variations may be made to the techniques described and illustrated herein without departing from the spirit and scope of the disclosure. Accordingly, it should be understood that the examples are illustrative only and are not limiting upon the scope of the disclosure.

EXAMPLES

Example 1: Gas Chromatography (GC) Analysis, Calculation of Conversion

1 µl of solvent phase (solvent-extracted sample) is injected (split ratio 3) onto a 30 m×0.32 mm×0.25 µm Zebron ZB-5 column. The column was developed at constant flow (4 ml/min $H_2$) with the temperature gradient: 100° C., 15° C./min to 200° C., 120° C./min to 240° C., 4 min at 240° C. Inlet temperature: 250° C., detector temperature: 250° C. (Thermo Trace 1310 GC apparatus).

Farnesylacetone conversion was calculated from the recorded substrate and product peak area as follows:

Conversion (%): 100×($Product_{peak\ area}$/ ($Product_{peak\ area}$+$Substrate_{peak\ area}$)

Example 2: BVMO Reaction on Farnesylacetone with Ethionamide Monooxygenase (EthA)

E. coli TOP10 transformed with the plasmid for EthA production (GenBank: AAK48336.1, UniProtKB P9WNF8, Fraaije et al. 2004, J. Biol. Chem. 279(5), 3354) was grown in 200 ml LB medium supplemented with 100 µg/ml ampicillin and 200 µg/ml FAD to an $OD_{650\ nm}$ of 0.75 (37° C., 200 rpm). Induction of enzyme production was then induced by addition of 0.2% arabinose. Farnesylacetone (0.1%) was added to the culture followed by incubation for a further 23 h at 30° C. The culture was sampled and extracted with methyl-t-butyl ether (MTBE) for GC analysis of substrate and product content. The identity of the reaction product was confirmed by GC-MS analysis. Conversion of Farnesylacetone to Homofarnesylacetate was 2-5% in two independent sets of experiments.

Example 3: BVMO Reaction on Farnesylacetone with Cyclopentadecanone Monooxygenase (CPDMO)

CPDMO was produced from E. coli BL21(DE3) cells transformed with a pJ401-derived plasmid for CPDMO production (GenBank AB232538.1, UniProtKB Q1T7B5).

200 ml LB medium culture (50 µg/ml kanamycin) was inoculated from an overnight seed culture, incubated at 28° C., 160 rpm for approx. 3.5 h to an $OD_{650\ nm}$ of 0.500-0.600. IPTG was added to 0.8 mM for induction of enzyme production. The culture was incubated for a further 3-4 h at 28° C., 160 rpm. The cells were harvested by centrifugation, and washed. The recovered cell pellet were suspended into 2.5 ml reaction buffer (50 mM Tris-Cl pH 9.0), the cells disrupted by sonication. To the sonicated material was finally added 16.5 ml 50 mM Tris-HCl pH 9.0, resulting into CPDMO crude enzyme preparation. For assaying enzyme activity was to 950 µl crude CPDMO enzyme preparation added 10 µl farnesylacetone and 40 µl 50 mM NADH. The reaction was incubated at 30° C. for 3 h, extracted with MTBE and GC-analyzed. Conversion of Farnesylacetone to Homofarnesylacetate was approx. 7%.

Example 4: BVMO Reaction on Farnesylacetone with EnzymeWorks BVMO Enzymes

Eight Baeyer Villiger Monooxygenase enzymes available from the enzyme supplier EnzymeWorks, Inc, (http://www.enzymeworking.com) were tested for their ability to convert farnesylacetone to homofarnesylacetate. The reactions contained 2 g/l Farnesyalcetone, 25 mM glucose, 1 mM NADP, 2 g/l BVMO enzyme, 2 g/l Glucose dehydrogenase (GDH), in 100 mM Glycine/NaOH buffer pH 9.0. The reactions were incubated at 30° C. for 24 with gentle shaking. (70 rpm). 0.5 ml reactions were extracted with 1.5 ml MTBE for GC analysis. Farnesylacetone conversion was approx. 50% in 24 h with EW-103 BVMO.

Example 5: BVMO Reaction on Farnesylacetone with Gecco-Biotech BVMO Enzymes

BVMO enzymes (wild type or variant enzymes) supplied by Gecco Biotech (http://www.gecco-biotech.com/) were applied to the conversion of farnesylacetone to homofarnesylacetate. The BVMO enzymes were provided as purified fusion proteins with phosphite dehydrogenase (PTDH). 20 mM farnesylacetone (approx. 5 g/l) were reacted for 20 hours at 24° C. in presence of 20 µM BVMO, 1 mM NADP and 100 mM $Na_2HPO_3 \cdot 5H_2O$ in 50 mM Tris HCl (pH 7.5) buffer (1 ml reaction volume).

The results summarized in the table below indicated between 3 and 52% farnesylacetone conversion depending on the BVMO enzyme used.

The abbreviations used in the table are "n.a.": not applicable. "STMO": Steroid monooxygenase. "PAMO": Phenylacetone monooxygenase. "HAPMO": 4-Hydroxyacetophenone monooxygenase. "ACMO": Acetone monooxygenase. "CPDMO": Cyclopentadecanone 1,2-monooxygenase.

| BVMO enzyme | Source microorganism | UniProtKB ID | Farnesylacetone conversion (%) |
|---|---|---|---|
| PAMO | Themobifida fusca | Q47PU3 | 7.9 |
| PAMO I67T | | n.a. | 4 |
| PAMO A442G | | n.a. | 5.1 |
| PAMO P440N | | n.a. | 5.2 |
| STMO | Rhodococcus rhodochrous | O50641 | 4.6 |
| HAPMO | Pseudomonas fluorescens | Q93TJ5 | 5 |
| ACMO | Gordonia sp. | A0A3G5BIW4 | 6.8 |

-continued

| BVMO enzyme | Source microorganism | UniProtKB ID | Farnesylacetone conversion (%) |
|---|---|---|---|
| MekA | *Pseudomonas veronii* | Q0MRG6 | 52.5 |
| CDMO | *Rhodococcus ruber* | Q938F6 | 8.4 |
| BpCHMO | *Brachymonas petroleovorans* | Q5VJE0 | 12 |
| Ocean | *Pseudooceanicola batsensis* | A3U3H1 | 12.6 |
| CPDMO | *Pseudomonas* sp. HI-70 | T2HVF7 | 3.8 |
| BVMO 24 | *Rhodococcus jostii* (strain RHA1) | Q0S5T2 | 3 |

Example 6: Cofactor Requirement of BVMO Enzyme EW-103

With EW-103 BVMO was investigated if both NADPH and NADH can act as cofactors in farnesylacetone conversion.

Reactions were run in 50 mM Tris-HCl buffer pH 8.5 with 7.6 mM Farnesylacetone, 1 mM cofactor, 2 mg/ml BVMO EW-103, 2 mg/ml GDH and 25 mM glucose (5 ml volume, Heidolph Synthesis 1, 30° C., 900 rpm). In one reaction was NADP substituted by NAD. Farnesylacetone conversion was supported by NADH as a cofactor but surprisingly stopped abruptly at approx. 20% conversion after two hours of incubation. Full farnesylacetone conversion was obtained in approximately the same time when NADPH was used as the cofactor.

The reaction was repeated using two different Glucose Dehydrogenase (GDH) enzymes as well as at increased NAD concentrations of (1, 2, and 5 mM). Independently of the NAD concentration applied and of the GDH enzyme used, Farnesylacetone conversion stopped at approximately 20% whereas again full conversion was achieved when NADPH was the cofactor (see FIG. 1).

Example 7: Cofactor Regeneration System

The use of a Glucose Dehydrogenase (GDH) or Alcohol dehydrogenase (ADH) when using glucose or isopropanol can be envisaged for cofactor regeneration. The possibility of using ADH/isopropanol instead of GDH/glucose was investigated, testing the sensitivity of EW-103 to isopropanol and acetone.

In a reaction run in 50 mM Tris-HCl buffer pH 8.5 with 7.6 mM Farnesylacetone (2 g/l), 1 mM NADP, 2 g/l BVMO EW-103, 2 g/l GDH and 25 mM glucose (5 ml, Heidolph Synthesis 1, 30° C., 900 rpm), isopropanol or acetone was added to 5% and 10% (v/v).

Figure 2:
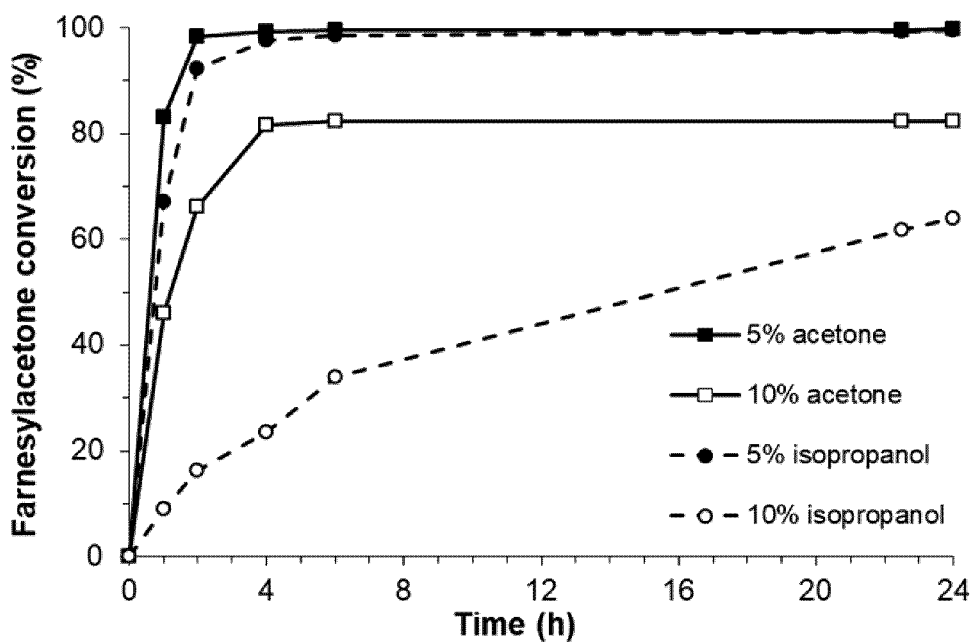
FIG. 2 shows the conversion over time of farnesylacetone in the presence of acetone or isopropanol at different concentrations.

The addition of 5% isopropanol or acetone to the reaction had no effect on farnesylacetone conversion. Farnesylacetone conversion decreased when isopropanol or acetone was added to 10%. When the reaction contained 10% isopropanol, farnesylacetone conversion was only around 64% in 24 h. EW-103 BVMO was less sensitive to acetone addition: farnesylacetone conversion was 80% in 24 h in a reaction containing 10% acetone (see FIG. 2).

This result indicated the possibility of using an Alcohol Dehydrogenase (ADH)/isopropanol cofactor regeneration system. ADH enzymes are available from many enzyme manufacturers and suppliers (as e.g. KRED-P2-H07 from Codexis Inc.)

The use of an ADH/isopropanol cofactor regeneration system was confirmed in a reaction run in 50 mM Tris-Cl buffer pH 8.5 with 8 g/l Farnesylacetone (30.5 mM) in presence of 1 mM NADPH, 1 g/L BVMO EW-103, 0.5 g/L ADH (Codexis KRED-P2-H07), 35 mM Isopropanol (150 mL total volume). Farnesyalcetone conversion was approx. 75% in 24 hours. In this reaction set up approx 6 g of farnesylacetone was converted to homofarnesylacetate with 1 g of EW-103 BVMO enzyme. This conversion yield was higher than in a similar experiment run using a GDH/Glucose cofactor regeneration system and where 1 g BVMO EW-103 enzyme was able to convert only 3.6 g of farnesylacetone.

Example 8: Reaction Products of BVMO Farnesylacetone Conversion

Homofarnesylacetate was identified by GC-MS analysis as the product of farnesylacetone conversion by the BVMO enzymes used.

In some reactions was interestingly and surprisingly observed both the production of homofarnesyalcetate and homofarnesol as reaction products. It is anticipated that this is the result of homofarnesylacetate hydrolysis due to a BVMO-independent reaction catalysed e.g. by a lipase (present in the enzyme lyophilisate or cell extract used). This was not investigated further but it can be anticipated that the oxidation step of farnesylacetone to homofarnesylacetate and the subsequent hydrolysis of homofarnesylacetate to homofarnesol can be catalysed in a one pot reaction combining the BVMO-catalysed reaction with e.g. an appropriate lipase-catalysed hydrolysis of homofarnesylacetate and applying adequate reaction conditions.

Example 9: Process-Relevant Reaction Conditions and Conversion Yield

Farnesylacetone conversion with EW-103 BVMO was run at 106 g/l substrate (0.4 M) in presence of 27 g/l isopropanol (0.44 M) with 9 g/l BVMO EW-103, 3.2 g/l ADH KRED-P2-H07 and 1.5 g/l NADPH (2 mM). The reaction was run in 50 mM Tris-Cl buffer pH 8.5 at 30° C. and with constant agitation. A reaction sample was extracted with MTBE for GC analysis. Farnesylacetone conversion was approx. 70% after 48 hours of reaction, corresponding to a conversion yield of 8 g of farnesylacetone per g of BVMO enzyme.

Further reactions were run at 106 g/l substrate (0.4 M) in presence of 27 g/l isopropanol (0.44 M), varying other reaction parameters: BVMO, ADH, and NADPH concentrations were set as follows:
 (1) 45 g/l, 10 g/l, 5 mM, or
 (2) 5 g/l, 10 g/l, 0.5 mM After approx. 24 hours of reaction the conversion of farnesylacetone was 86.2% in (1) representing a conversion yield of 2 g farnesylacetone per gram of BVMO enzyme as judged from a reaction sample extracted with MTBE. In (2) the conversion of farnesylacetone was 59% as judged from a reaction sample extracted with MTBE, corresponding to a conversion yield of approx. 12.5 g farnesylacetone converted per gram of BVMO enzyme.

This result demonstrated that the probability was high to fully convert farnesylacetone with a BVMO enzyme (e.g. BVMO EW-103) in approx. 24 hours, and that carefully setting enzyme to substrate ratio would increase conversion yield defined as g substrate converted per gram of BVMO enzyme and productivity defined in terms of farnesylacetone conversion per gram BVMO enzyme and hour of reaction.

Example 10: Conversion of Ethylfarnesylacetone with a BVMO Enzyme

Ethylfarnesylacetone (mixture of four isomers) was submitted to BVMO oxidation with EnzymeWorks BVMO EW-103. The reaction (5 ml volume) contained 2 g/l substrate, 2 g/l BVMO enzyme, 0.5 g/l NADP, 4.5 g/l glucose, 2 g/l GDH in 50 mM Glycine/NaOH buffer pH 9.0. The reaction was incubated at 30° C., 650 rpm (Heidolph Synthesis 1 apparatus). The reaction was sampled 5, 12.5 and 48 h after start, extracted (0.6 ml reaction to 0.7 ml MTBE) and analysed for substrate/product content by GC-FID. Four reaction products were identified from four isomer substrate peaks. GC-MS analysis identified that ethylfarnesylacetone was converted to homoethylfarnesylacetate. Overall 25-30% conversion was observed.

Further hydrolysis of the reaction product homoethylfarnesylacetate e.g. using, for example, a lipase enzyme would produce Ethylhomofarnesol, the substrate for cyclization to Ethylambrofix with a Squalene Hopene Cyclase (SHC) enzyme.

Example 11: Ethylfarnesylacetone

A solution of ethyl magnesium bromide in diethyl ether (3 M, 175 mL, 525 mmol, 1.2 equiv.) was added dropwise to the solution of 5,9-Dimethyldeca-4,8-dienal (E/Z-mixture, 78.8 g, 437 mmol) in diethyl ether (200 mL) at −50° C. during 30 min. After complete addition the cooling bath was removed and the mixture was stirred for one hour. Then it was poured on 2 M aq. HCl solution (200 mL) and the mixture was extracted with methyl t-butyl ether (MTBE, 150 mL). The organic layer was washed with water and diluted aq. NaCl solution to pH-neutrality and dried over $MgSO_4$. After filtration and removal of the solvent in a rotary evaporator, a clear colourless liquid was obtained (79.2 g, 86%), which was dissolved in acetone (200 mL). After cooling to 0° C., Jones reagent (4 M $CrO_3$ in aqueous $H_2SO_4$, 94.1 mL), was added dropwise, during which the temperature rose to 43° C. and the mixture turned to a green-brown colour. After finished addition, the mixture was stirred at room temperature for 1 h, then an additional amount of Jones reagent was added (30 mL) and stirring was continued for 20 min, then 2-propanol was added (20 mL). Workup and extraction were effected as above to yield a clear yellow liquid (74.8 g), which distilled at 91-95° C. (0.09 mbar) over a 10 cm Vigreux column to yield 7,11-dimethyldodeca-6,10-dien-3-one (50.1 g, 64%, E/Z-mixture) as a slightly yellow, clear oil.

A solution of 7,11-dimethyldodeca-6,10-dien-3-on (34.0 g, 163 mmol) in THF (100 mL) was added at −5° C. during 30 min to a freshly prepared solution of vinyl magnesium bromide in THF (0.9 M, 228 mmol, 1.4 equiv.). The resulting mixture was stirred at room temperature for 20 min, and then hydrolysed by addition of sat. aq. $NH_4Cl$-solution (150 mL). Further workup was effected as above to yield a clear, yellow liquid (37.5 g), which was purified by distillation over a 10 cm Vigreux column to yield 3-ethyl-7,11-dimethyldodeca-1,6,10-trien-3-ol distilling at 90° C./0.07 mbar (12.0 g, 31%, clear colourless liquid, E/Z ratio 5:4 according to GC).

To this product (12.0 g, 50.8 mmol) was added 2-methoxy propene (7.33 g, 102 mmol, 2 equiv.) and phosphoric acid (10 mg). The mixture was placed in an autoclave vessel and stirred at 170° C. for 3 h. After cooling to room temperature, the same amounts of 2-methoxy propene and phosphoric acid as mentioned above were added and the mixture was stirred at 170° C. for 18 h. After cooling to room temperature, the mixture was concentrated in a rotary evaporator to yield a brown liquid (14.91 g), which was distilled in a Kugelrohr oven at 150° C./0.05 mbar to yield a clear yellow liquid (12.66 g) which was further purified by flash chromatography on silica gel with heptane/MTBE 95:5 to yield 6-ethyl-10,14-dimethylpentadeca-5,9,13-trien-2-one (6.51 g, 46%) as a colourless liquid (mixture of E/Z isomers, 31/26/25/18% according to GC).

$^1$H-NMR (CDCl$_3$, 400 MHz): 4.88-5.37 (m, 3H), 2.46 (d, J=7.8 Hz, 2H), 2.29 (br d, J=7.8 Hz, 2H), 2.15 (s, 3H), 1.96-2.11 (m, 10H), 1.67-1.73 (m, 5H), 1.60-1.65 (m, 4H), 0.94-1.03 (m, 3H). $^{13}$C-NMR (CDCl$_3$, 101 MHz): 208.8 (s), 208.7 (s), 142.3 (s), 142.2 (s), 142.1 (s), 135.3 (s), 135.2 (s), 135.1 (s), 135.0 (s), 131.5 (s), 131.3 (s), 131.3 (s), 124.7 (d), 124.3 (d), 124.2 (d), 124.0 (d), 122.0 (d), 121.6 (d), 121.5 (d), 44.1 (t), 39.7 (t), 39.7 (t), 36.8 (t), 36.5 (t), 32.0 (t), 32.0 (t), 31.9 (t), 30.6 (t), 30.3 (t), 30.0 (q), 29.9 (q), 29.5 (t), 26.9 (t), 26.8 (t), 26.7 (t), 26.7 (t), 26.6 (t), 26.6 (t), 25.7 (q), 25.7 (q), 23.4 (q), 23.4 (q), 23.1 (t), 23.1 (t), 22.7 (t), 22.2 (t), 22.1 (t), 17.7 (q), 17.6 (q), 16.0 (q), 16.0 (q), 14.1 (q), 13.2 (q), 13.2 (q), 12.8 (q). MS (EI, 70 eV): 276 (M$^+$, <1), 218 (<1), 207 (<1), 149(10), 136(15), 121(28), 107(10), 95(16), 81(36), 69(89), 55(15), 43(100).

The invention claimed is:

1. A method of producing an acetate of formula (I)

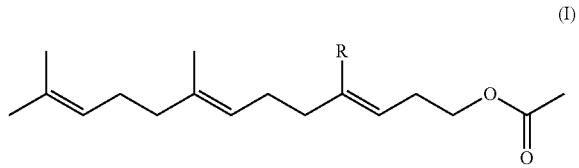

wherein R is methyl or ethyl,
from ketone of formula (II)

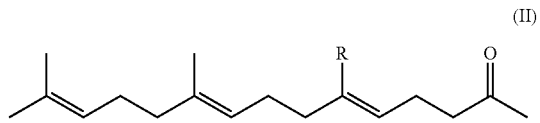

wherein R has the meaning given above,
the method comprising contacting the compound of formula (II) with a Baeyer-Villiger monooxygenase (BVMO) enzyme in the presence of a cofactor.

2. The method of claim 1, wherein the cofactor is selected from NADH, NADPH, or a combination thereof.

3. The method of claims 1, further comprising the presence of a cofactor regeneration system.

4. The method of claim 3, wherein the cofactor regeneration system comprises alcohol dehydrogenase enzyme and isopropanol.

5. The method of claims 1, wherein the method further comprises hydrolysis of the acetate of formula (I) to an alcohol of formula (III)

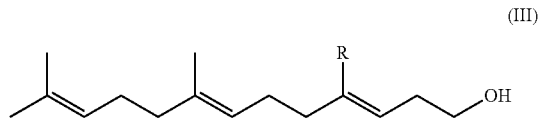

wherein R is methyl or ethyl.

6. A method of utilizing the alcohol of formula (III) of claim 5 for producing a fragrance ingredient.

7. The method of claim 1, wherein the BVMO enzyme is derived from a microorganism selected from the group consisting of *Pseudomonas sp., Rhodococcus sp., Brevibacterium sp., Comanonas sp., Acinetobacter sp., Arthrobacter sp., Brachymonas sp., Themobifida sp., Gordonia sp.*, and *Pseudooceanicola sp.*

8. The method of claim 1, wherein the amount of the BVMO enzyme and the cofactor is about the same.

9. The method of claim 1, wherein R is methyl.

10. The method of claim 3, wherein the cofactor regeneration system comprises at least one of glucose dehydrogenase enzyme and glucose or phosphite dehydrogenase enzyme and sodium phosphite.

11. The method of claim 2, further comprising the presence of a cofactor regeneration system.

12. The method of claim 11, wherein the cofactor regeneration system comprises alcohol dehydrogenase enzyme and isopropanol.

13. The method of claim 11, wherein the cofactor regeneration system comprises at least one of glucose dehydrogenase enzyme and glucose or phosphite dehydrogenase enzyme and sodium phosphite.

* * * * *